United States Patent [19]
Perisse

[11] 4,038,988
[45] Aug. 2, 1977

[54] SURGICAL APPARATUS

[76] Inventor: Pierre Perisse, 8, rue du Stade, 31370 Rieumes, France

[21] Appl. No.: 645,561

[22] Filed: Dec. 31, 1975

[51] Int. Cl.² .............................................. A61B 17/12
[52] U.S. Cl. ...................................... 128/326; 289/2
[58] Field of Search ............... 128/326, 334 R, 325, 128/320, 327, 346; 289/2

[56] References Cited
U.S. PATENT DOCUMENTS
3,856,018  12/1974  Perisse et al. ...................... 128/326

FOREIGN PATENT DOCUMENTS
2,229,377  12/1974  France .............................. 128/326

Primary Examiner—Robert W. Michell
Assistant Examiner—Michael H. Thaler
Attorney, Agent, or Firm—J. Harold Nissen

[57] ABSTRACT

Surgical apparatus to ligature sectioned blood vessels automatically comprising a tubular body provided with two angularly offset longitudinal grooves, a tubular spindle fitted within the body and adapted to carry two or more suture-holding cartridges, one end of the spindle being adapted for connection to a vacuum source, and a spring on the spindle to urge the cartridges to the opposite end of the spindle, the cartridges include two relatively rotatable members which have studs adapted to be guided in the longitudinal grooves so that the suture is automatically tightened and the ends thereof are cut off.

10 Claims, 9 Drawing Figures

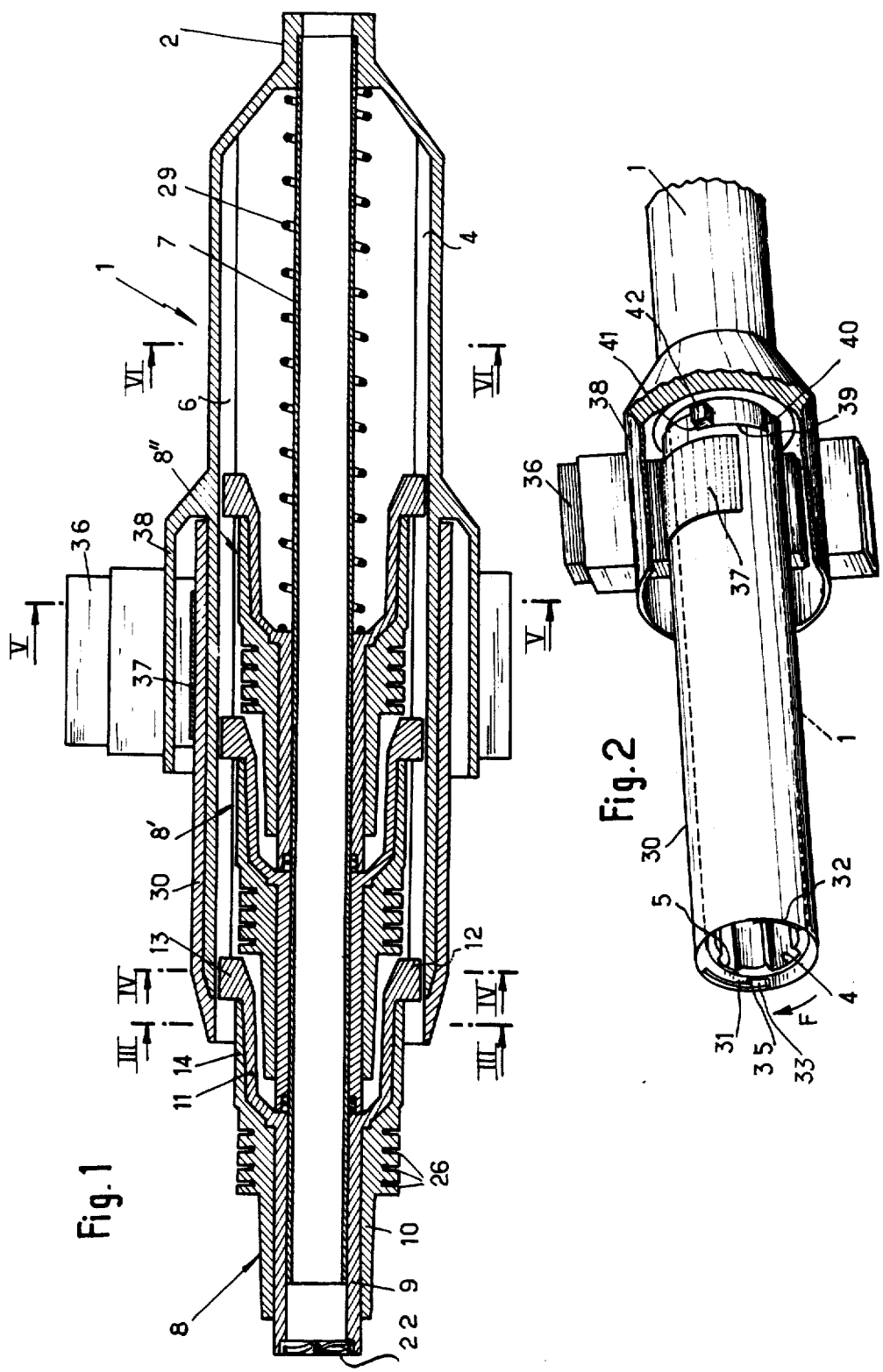

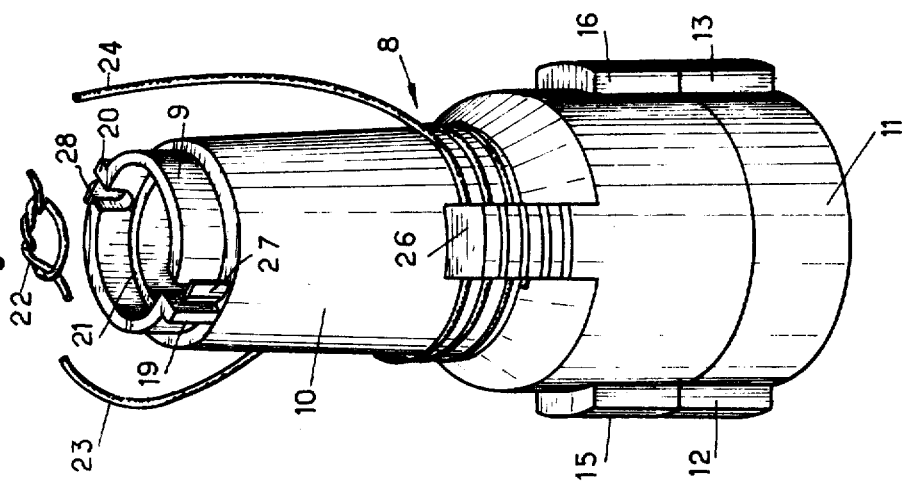
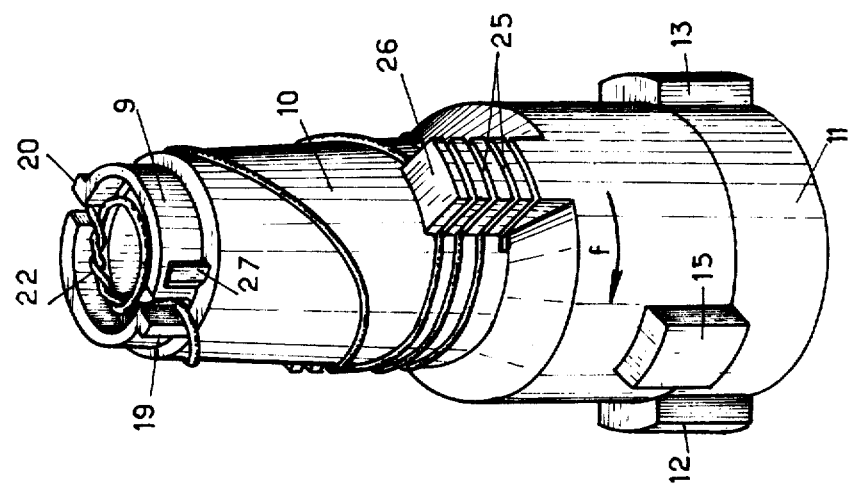
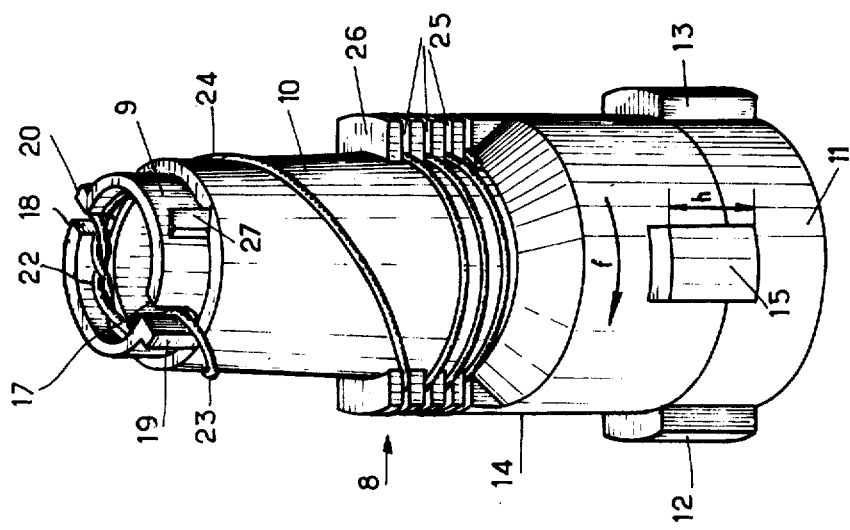

SURGICAL APPARATUS

The present invention relates to a surgical apparatus adapted for the repetitive and automatic ligature of sectioned blood vessels.

From French Patent Application No. 73 17411 filed on 14th May 1973, now French Pat. No. 2,229,377, an apparatus is already known which satisfies this function, but which has the disadvantage of being expensive. Well, it is highly desirable to use the appliance only for a single surgical operation and to throw it away after the operation, since it is quite impossible to sterilise it into its tiniest corners for re-use.

The object of the invention is to provide a surgical apparatus which has all the qualities of that according to the abovementioned Patent Application but which is of simpler construction and the prime cost of which is far lower, so that one apparatus can be used for each surgical operation.

According to the invention, the surgical apparatus is characterised in that it comprises a tubular body having on its inner wall at least two angularly offset longitudinal grooves which extend over the entire length of the body, a rigid tubular spindle disposed according to the axis of the body and fitted in sealing-tight fashion at one end of the body to which a vacuum source is connected; several suture-holding cartridges threaded onto the rod and biased en bloc by a spring urging them towards the other end of the body, each cartridge being composed of two coaxial tubular members which are capable of turning one with repect to the other and provided with flanges of the same diameter each carrying a stud on its outer wall, the two studs being mounted to slide in the said grooves, the internal tubular member or journal carrying a preformed suture, the ends of which are fixed on the outer tubular member or sleeve and are so dimensioned that, when the said studs are in their respective grooves, the suture is wide and may therefore be applied around the zone where the blood vessel to be ligatured is located and so that, when the studs are brought into alignment by rotation of the sleeve about the journal, the suture is completely closed and ties off the base of the knob of tissue drawn in at the end of the tubular spindle, sectioning means causes to rotate by the sleeve being provided to cut off the said ends when the suture is tightened; a tubular sleeve mounted to rotate about the second end of the tubular body and comprising on the one hand a frontal stop which projects from the inside wall of the sleeve and which extends in an arc of a circle of sufficient amplitude to intercept only the stud on the sleeve of the outermost cartridge and furthermore a lateral stop rigid with the sleeve and which, when this latter is caused to rotate, is able to rotate the sleeve of the outer cartridge around the journal, bearing on the stud on the inner sleeve, until such time as the two studs are brought into alignment; and an elastically returned manual operating member adapted to cause the said sleeve to rotate.

Thus, by a simple biasing of the manual operating member, rotation of the sleeve about the tubular member is caused, the simultaneous effects of which are to rotate the socket of the first cartridge around the journal and thus to tighten the preformed suture around the base of the knob of tissue formed by suction into the end of the tubular spindle and the cutting off of the ends of the suture, expulsion of the said first cartridge out of the apparatus and its replacement by a new cartridge which is loaded with a suture.

In contrast to the apparatus of the prior art mentioned hereinabove, the apparatus according to the invention comprises no complicated parts such as a piston, requiring accurate machining. On the contrary, all its constituent parts, including the cartridges, are very simple and may be produced by moulding, for example in a plastics material. Therefore, it becomes possible to produce the applicance in series, and therefore at sufficiently low prime costs that the apparatus may be used ones only.

A form of embodiment of the apparatus according to the invention will now be described by way of non-limitative example, with reference to the appended drawings in which:

FIG. 1 is a longitudinal sectional view through the apparatus;

FIG. 2 is a partial perspective view of the apparatus, with part torn away;

Figure 3:
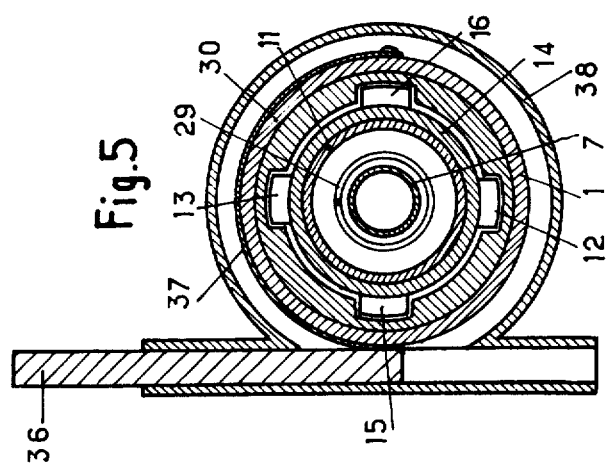
FIGS. 3 to 6 are cross-sectional views respectively on the lines III—III, IV—IV, V—V and VI—VI in FIG. 1, and FIGS. 7 to 9 are perspective views of a suture-carrying cartridge in three successive positions of operation of the apparatus.
Figure 4:
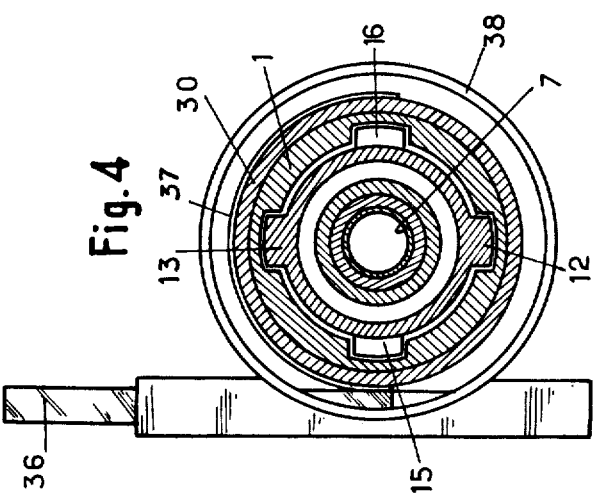
Figure 6:
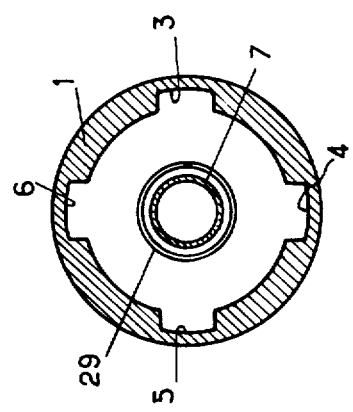
Figure 5:
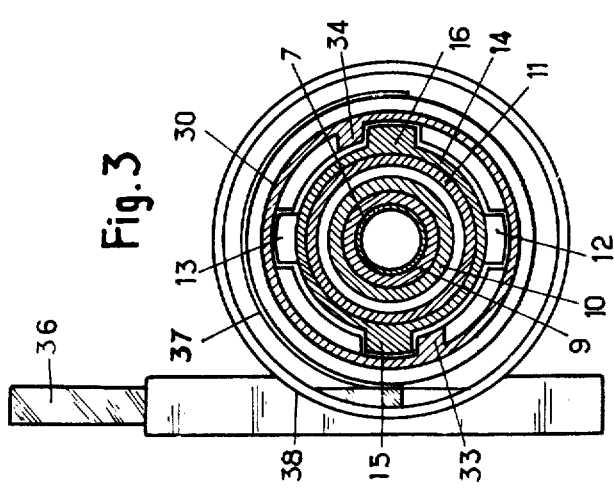

With reference to FIGS. 1 to 6, the surgical apparatus comprises a moulded tubular body 1 open at one end and narrowing at the other end to form a connector 2 on which may be fitted a pipe connected to a vacuum source, not shown. The body has on its inner wall four longitudinal grooves 3 to 6 which are staggered at 90° with respect to one another and they extend over the entire length of the body. Inside this latter there is a rigid tubular spindle 7, one end of which is fitted in sealing-tight manner in the connector 2. The space inside the body 1 serves as a load container adapted to accommodate several suture-carrying cartridges 8, 8', 8", which are mounted to slide along the spindle 7.

As FIGS. 1 and 7 to 9 show, each cartridge comprises two tubular members: a tubular journal 9 and a coaxial bush or sleeve 10 mounted to rotate loosely about the journal. The journal and the bush are made by moulding, for example in a plastics material. The journal 9 has an inside diameter which is slightly larger than the outside diameter of the spindle 7 so that the cartridge is free to slide along the spindle. At the end of the journal is a flange 11 of widened diameter, carrying on its outer wall two diametrically opposed studs 12, 13. Likewise, the sleeve 10 ends in a flange 14 having an outside diameter substantially equal to that of the flange 11. The sleeve also carries two studs 15, 16 which are diametrically opposed. At the opposite end from the flange 11, the journal 9 projects out of the sleeve 10, the projecting edge being notched at two diametrically opposed points 17, 18. The notches are edged on one of their faces by abutments 19, 20 which project outwardly and of which one of the functions is to prevent the axial sliding of the sleeve with respect to the journal. Another function of these stops will be revealed hereinafter.

On its inner wall, at the end of the cylindrical portion, the journal 9 has a shoulder 21 (FIG. 9) which is turned towards the said end, and on which initially rests an opened-out preformed suture 22 of suture thread. The two ends 23, 24 of the suture pass respectively through notches 17, 18, are folded back over stops 19, 20 and are anchored in that they are wound several times within notches 25 formed on the outer wall of the sleeve 10. In the form of embodiment described, the notches are disposed between adjacently disposed projections 26 which are moulded with the sleeve.

The sleeve or bush comprises on its inner wall two diametrically opposed longitudinal grooves in which are respectively inserted two blades 27, 28, one end of which extends beyond the end of the bush 10.

Initially, the cartridge is in the position shown in FIG. 7 in which the suture 22 is of a diameter substantially equal to the inside diameter of the end of the journal 9 and in which the studs 15, 16 are set crosswise with respect to the studs 12, 13. As the bush 10 is pivoted in the direction of the arrows $f$, in FIGS. 7 and 8, a pull is applied to the ends 23 and 24 and the suture 22 becomes retightened. The disposition is such that, at the moment when the studs 15 and 16 are respectively aligned with the studs 12, 13, the blades 27, 28 cut off the ends 23 and 24 of the suture, the stops 19, 20 then serving as support surfaces.

With reference again to FIGS. 1 to 6, a plurality of cartridges 6 (three in the case of FIG. 1) threaded on the spindle 7, are introduced into the interior of the body 1, the studs 12, 13, 15 and 16 being respectively fitted into the grooves 4, 6, 5 and 3. The assembly of cartridges is urged elastically towards the open end of the tubular body by a coil spring 29.

In order to hold the cartridges inside the body and in order to be able to release them one by one, the invention provides for a tubular sleeve 30 to be mounted to rotate about the open end of the body. The sleeve extends slightly beyond the said end and formed on the inner wall of the protruding portion (FIG. 2) are two frontal stops 31, 32 in an arc of a circle, diametrically opposed and having an angular magnitude substantially equal to the angular offset between two consecutive grooves in the body 1, for example the grooves 4 and 5. Each frontal stop comprises a thickened end 33, 34 (FIGS. 2 and 3) forming a stop.

The sleeve 30 is pushed onto the body 1 until the stops 33, 34 come in contact with the outer edge of the body. Between the said edge and the frontal stops 30, 32 there are then two gaps such as 35 (FIG. 2), the width of which measured in the longitudinal direction of the body, is slightly larger than the height h of the studs 15, 16 of the sleeve 10. Thus, the outermost cartridge 8 of the stock projects outside the sleeve, but it is held inside the body by locking of the studs 15, 16 of the bush 10 against the frontal stops 31, 32. In this position, the studs 15, 16 are entirely within the previously defined gaps 35 and are therefore free of the grip of grooves 3 and 5, while the studs 12, 13 of the journal 9 are still fitted in the grooves 4 and 6.

In order to rotate the bush 10 about the journal 9, a suitable operating means is provided according to the invention, for example a push button 36 which is rigid with a semi-annular leaf spring 37 which is wound around the sleeve and one end of which is fixed to this latter by any appropriate means. The push button is mounted to slide in a plane tangent to the sleeve, inside a cylindrical casing 38 moulded together with the tubular body 1. As FIG. 2 shows, the sleeve 30 comprises at its end opposite that on which the stops 31, 32 are formed, a peripheral notch 39 bounded by two shoulders 40, 41. The size of the notch is substantially equal to 90°. A stop 41 moulded with the body 1 is engaged in the notch and thus limits the rotary movement of the sleeve to a quarter of a turn. The stop is positioned so that in the position of rest shown in FIG. 2, the frontal stops 31, 32 are opposite grooves 3 and 5, the possible direction of rotation of the sleeve being indicated by the arrow F.

The apparatus according to the invention functions as follows:

The apparatus is supplied fully loaded and it can be used until its stock of cartridges is exhausted, whereupon it is thrown away. In its position of rest, it is as shown in FIGS. 1 and 2: the sleeve 30 has its shoulder 41 abutting against the stop 42, the leaf spring 37 is relaxed and the push button 36 is in the extended position. Furthermore, the cartridge 8 partially projects outside of the sleeve 30, its studs 12, 13 being engaged in the end of grooves 4, 6 and its studs 15, 16 being completely clear of the grooves 5, 3 and biased to bear against the frontal stops 31, 32.

The apparatus is gripped like a fountain pen, by the rear part of the body 1. In order to make a ligature, the projecting end of the cartridge 8 is applied to the area of tissues comprising the sectioned blood vessel. In view of the fact that the inside of the spindle 7 is connected to a vacuum source, a knob of tissue is drawn into the journal 9 of the cartridge 8. With the index finger, for example, the push button 36 is depressed, rotating the sleeve 30 in the direction of the arrow F, through the leaf spring 37 which becomes tensioned. In this rotary movement, the thickened ends 33, 34 of the stops 31, 32 cause the bush 10 of the cartridge 8 to rotate, acting on the studs 15, 16. The journal 9 is immovable during this movement in view of the fact that its studs 12, 13 are engaged in the grooves 4, 6. The pressure on the push button is maintained until such time as this latter has turned through approximately a quarter of a turn. At this moment, the shoulder 40 of the sleeve comes in contact with the stop 42. During this time, the journal has turned in the direction of the arrow $f$, as shown in FIGS. 7 to 9. The suture 22 is progressively tightened, constricting the bottom of the sucked in knob of tissue. When the sleeve has reached the end of its rotary movement, the studs 15 and 16 are aligned with the studs 12, 13 (FIG. 7), the suture is completely tightened and the ends 23, 24 of the stitch are cut off by the blades 27, 28: the blood vessel is ligatured. The cartridge 8 cannot however yet be expelled from the body 1 in view of the fact that the frontal steps are still retaining the studs 15, 16 and 12, 13. To eject the cartridge 8, it is sufficient to release the push button 36: the tensioned leaf spring 37 abruptly returns the sleeve 30 to its initial position, causing it to rotate in the opposite direction to the arrow F. In this movement, the portions 33 and 34 do not act on the studs 15, 16 which remain aligned with the studs 12, 13. As soon as the frontal stops are no longer opposite the grooves 4, 6, the cartridge 8 which is no longer held is ejected by the thrust of the pretensioned spring 29. The cartridge 8' then takes the place of the cartridge 8 and the appliance is ready for a fresh ligature.

Thus, by depressing the push button and then releasing it, the stitch is tightened, the ends of the stitch are cut off, the used cartridge is ejected and is replaced by a fresh cartridge.

The appliance according to the invention is therefore simple to operate. Thanks to the simplicity of its structure, it is inexpensive and can therefore be thrown away after one surgical operation.

I claim:

1. Surgical apparatus for carrying out a ligature of sectioned blood vessels, repetitively and automatically, comprising a tubular body (1) having on its inside wall at least two longitudinal grooves (3, 4) and/or (5, 6) which are angularly offset and which extend over the entire length of the body, a rigid tubular spindle (7) disposed according to the axis of the body and having first and second ends, said first end being fitted in sealing-tight manner to one end (2) of the body, said one end of said body having an orifice in alignment with said spindle, and adapted to be connected to a vacuum source at said orifice, said second end forming a stem, several suture carrying cartridges (8, 8', 8"), fitted onto said stem and biased en bloc by a spring (29) mounted around said stem and between said one end of said body and the innermost cartridge, urging said cartridges towards the other end of the body, each cartridge being composed of two coaxial tubular members (9, 10) capable of turning one with respect to the other and provided with flanges (11, 14) of the same diameter, each carrying on its outer wall at least one stud (12, 15) and/or (13, 16), the two studs being mounted to slide in the longitudinal grooves mentioned, the internal tubular member or journal (9) carrying a preformed suture (22), the ends of which (23, 24) are fixed on the outer tubular member or bush (10), being so dimensioned that, when the said studs are in their respective grooves, the suture is opened out and may thus be applied around the zone where the blood vessel to be ligatured is located and so that, when the studs are brought into alignment by rotation of the bush about the journal, the suture is completely tightened and constricts the base of the knob of tissue drawn in at the end of the tubular spindle (7), sectioning means (27, 28) mounted on the bush and being provided to cut off the said ends when the suture has been tightened, a tubular sleeve (30) mounted to rotate about the said other end of the tubular body, at least one frontal stop (31) and/or (32) projecting from the inside wall of the sleeve, said sleeve extending beyond said other end of said body, said stop extending in an arc of a circle of sufficient amplitude to intercept only the stud on the bush of the outermost cartridge, and moreover, at least one lateral stud (33) rigid with the sleeve and which, when this latter is caused to rotate, is capable of turning the bush (10) of the outermost cartridge (8) around the journal (9), bearing on the stud (15) of the bush, until the two studs (12, 15) are brought into alignment, and an elastically returned manual operating means (36) adapted to rotate the said sleeve (30).

2. Surgical apparatus according to claim 1, wherein the lateral stud (33) is constituted by a thickened end of the frontal stop (31).

3. Surgical apparatus according to claim 2, wherein said body has four longitudinal grooves (3 to 6) offset by 90° on the inner wall of the tubular body, and the journal (9) and the bush (10) of each cartridge (8) are each provided with two studs (12, 13 and 15, 16) which are diametrically opposed and the sleeve (30) comprises two frontal stops (31, 32) and two lateral studs (33) disposed to act on the two studs (15, 16) of the bush of the outermost cartridge (8).

4. Surgical apparatus according to claim 1, wherein the journal (9) of the cartridge extends over the bush (10) at the end opposite the flange, the projecting end of the journal having two notches (17, 18) which are diametrally opposed and into which fit the ends (23, 24) of the preformed suture (22) which is disposed concentrically of the journal (9) and on the inside of this latter, the said ends being coiled about the bush (10) of the cartridge and being anchored against sliding in a plurality of notches (25) formed on the outer wall of the bush (10).

5. Surgical apparatus according to claim 4, wherein the sectioning means consist of two cutting blades (27, 28) inserted in two longitudinal diametrically opposed grooves formed on the inside wall of the bush (10), the said blades extending at the end of the bush to the level of the points of emergence of the ends (23, 24) from the notches (17, 18) in the journal (9).

6. Surgical apparatus according to claim 1, wherein the manual operating means consists of a push button (36) mounted to slide tangentially of the sleeve (30) inside a casing rigid with the tubular body, the said push button causing the sleeve to rotate by virtue of a leaf spring (37) wound around the sleeve and the ends of said leaf spring which are rigid with said sleeve and with said push button.

7. Surgical apparatus according to claim 1, wherein the amplitude of the rotation of the sleeve (30) needed to bring the studs (15, 16) on the bush (10) into alignment with those (12, 13) of the journal (9) is defined by the co-operation of a fixed stop (42), formed on the outer wall of the tubular body (1) and the shoulders of a notch (39) formed at the end of the sleeve (30) opposite that which carries the frontal stops (31, 32).

8. Surgical apparatus according to claim 1, wherein
said body has four longitudinal grooves offset by 90° on the inner wall of the tubular body;
said journal and said bush of each cartridge are each provided with two studs which are diametrically opposed;
said sleeve comprises two frontal stops and two lateral studs disposed to act on said two bush studs of the outermost cartridge, said lateral studs each having a thickened end; and
said tubular body includes a fixed stop formed on the outer wall thereof, and said sleeve has a notch formed at the end thereof opposite to said frontal stops, the amplitude of the rotation of said sleeve required to bring said bush studs into alignment with said journal studs being defined by the cooperation of said fixed stop with said sleeve notch.

9. Surgical apparatus according to claim 8, wherein the manual operating means includes:
a push button mounted to slide tangentially of said sleeve inside a casing rigid with said tubular body, and
a leaf spring wound around said sleeve, the ends of which are rigid with said sleeve and with said push button, said push button cooperating with said leaf spring to rotate said sleeve.

10. Surgical apparatus according to claim 8, wherein
the journal of the cartridge extends over the bush at the end opposite said flange, the projecting end of the journal having two notches which are diametrically opposed and into which the ends of the preformed suture fit;
said bush having a plurality of notches in the outer wall thereof to anchor the suture against sliding; and,
said sectioning means comprising two cutting blades inserted in two longitudinal diametrically opposed grooves formed on the inside wall of said bush, said blades extending at the end of said bush to the level of the points of emergence of the ends of the suture from said journal.

* * * * *